United States Patent [19]

Jassawalla

[11] 4,273,121
[45] Jun. 16, 1981

[54] MEDICAL INFUSION SYSTEM

[75] Inventor: Jal S. Jassawalla, San Francisco, Calif.

[73] Assignee: Andros Incorporated, Berkeley, Calif.

[21] Appl. No.: 79,806

[22] Filed: Sep. 28, 1979

Related U.S. Application Data

[63] Continuation-in-part of Ser. No. 878,700, Feb. 17, 1978, Pat. No. 4,199,307, which is a continuation-in-part of Ser. No. 812,904, Jul. 5, 1977, abandoned.

[51] Int. Cl.³ .............................................. A61M 5/00
[52] U.S. Cl. ........................ 128/214 F; 128/DIG. 12; 417/474; 417/478; 417/479; 417/480
[58] Field of Search ....... 128/214 E, 214 F, DIG. 12, 128/DIG. 13, 273; 417/474, 478, 479, 480; 222/55, 92, 95, 96, 97, 214; 92/102

[56] References Cited

U.S. PATENT DOCUMENTS

| 3,336,843 | 8/1967 | Griswold | 92/102 X |
| 3,518,033 | 6/1970 | Anderson | 417/478 |
| 3,778,195 | 12/1973 | Bamberg | 417/474 |
| 4,126,132 | 11/1978 | Portner et al. | 128/214 F |
| 4,142,524 | 3/1979 | Jassawalla et al. | 128/214 F |

FOREIGN PATENT DOCUMENTS 1911919 9/1970 Fed. Rep. of Germany .......... 417/479

Primary Examiner—Peter A. Hruskoci
Assistant Examiner—David R. Sadowski
Attorney, Agent, or Firm—Fitch, Even, Tabin, Flannery & Welsh

[57] ABSTRACT

A medical infusion system is described employing a pump for conducting fluid or semi-solids from an upstream portion to a downstream portion of the system. The pump includes upstream and downstream conduit means and a removable cassette communicating between the two. The cassette has a window therein and a diaphragm spans the window. The cassette has inlet and outlet openings valvelessly communicating with the pumping chamber or cavity of the cassette. Fluid in the conduit is pumped by restricting and opening the conduit means at upstream and downstream locations, and displacing the contents of the cassette pumping chamber appropriately.

5 Claims, 7 Drawing Figures

MEDICAL INFUSION SYSTEM

This application is a continuation-in-part of application Ser. No. 878,700, filed Feb. 17, 1978, now U.S. Pat. No. 4,199,307, which was a continuation-in-part of application Ser. No. 812,904 filed July 5, 1977, and now abandoned. This invention relates to medical infusion systems and, more particularly, to an improved pump and cassette for use therein.

Various medical infusion systems for the delivery of fluids or semi-solids into a patient are well known in the prior art, and such systems are in widespread daily use in hospitals throughout the world. These systems are commonly used for such things as the intravenous or intra-arterial delivery of glucose solutions and blood plasma, for the delivery of drugs, and for enteral delivery of fluids and semi-solids. Typically, delivery is at controlled rates depending on the patient's needs, and in the case of drugs, the drug concentration being delivered is controlled.

A commonly used form of infusion system for intravenous delivery of fluids is comprised of a fluid container, a drip chamber and an adjustable clamp in the tube leading from the drip chamber to the needle penetrating the vein. The fluid container or bottle is supported at an elevated position with respect to the patient, with the drip chamber typically immediately thereunder. Transparent walls in the drip chamber coupled with a fixed volume of air therein allows the visual determination of the drip rate, which in turn is adjustable by the hose clamp. Thus, as fluid being delivered seeps past the pinched area of the hose, the air pressure in the drip chamber decreases, thereby encouraging the formation and dislodging of a drop from the tip of the small tube into the drip chamber coupled to the bottle.

For a number of reasons, it may be advantageous from a medical standpoint to utilize some type of pump in an infusion system, rather than relying upon the gravity drip type system described above. Some advantages from utilizing a pump include the ability to control and vary the flow rate every precisely and the ability to obtain much more accurate control over dosage.

To this end, various types of medical infusion systems utilizing pumps have been developed. The types of pumps employed have included the well known peristaltic pump principle. Such pumps, however, have suffered from poor accuracy and reproducibility, are typically relatively complex in their structural design, and have relatively high power requirements, making them typically unsuitable for portable battery-powered operation.

The so-called syringe type pump, which is akin to the common medical syringe, has also been utilized in pump type medical infusion systems. Syringe type pumps, however, are typically relatively expensive and present difficulties in their control and in the refilling operation. In this latter connection, cleaning of the syringe chamber is often cumbersome and time-consuming.

A medical infusing system employing a pump which incorporates some of the characteristics of both the peristaltic pump and the syringe type pump has been developed. A system employing such a pump is shown and described in U.S. Pat. No. 3,778,195. Such pumps have not been widely utilized in medical infusion systems due to their relatively poor accuracy and the difficulty of reproducibility of results. Moreover, such pumps are typically hard to clean and refill.

A number of medical infusion systems have recently been developed which employ disposable cassettes having rigid walls defining a pumping chamber or cavity and having a membrane or other deformable member for varying the volume of the pumping chamber. Valves are incorporated at the inlet and outlet ports of the pumping chamber so that when the volume of the pumping chamber is reduced, fluid therein is expelled through the outlet port and so that when the volume of the pumping chamber is increased, fluid is drawn into the pumping chamber through the inlet port. Because the cassette which forms the pumping chamber or cavity is replaceable, a new cassette may be used for each patient and type of fluid. Thus, sterility can easily be assured and cross contamination easily avoided.

Cassette type pumps, however, have a number of disadvantages in the prior known configurations. In particular, the replaceable cassettes for the pumps are often relatively expensive and must be fabricated from a relatively large number of close tolerance parts. Aside from such elements as coiled springs and close fitting moving parts for check valves, such pumps sometimes employ metal parts which must be protected against corrosion, etching and other adverse effects thereon which may result in dissolved materials being infused.

Another and perhaps more significant disadvantage of cassette type pumps as described above is their inherent limitation on continuity of flow rate. Because the valves operate passively, that is, in response to pressure changes in the pumping chamber, a displacement stroke which varies the volume of the pumping chamber and thus the pressure therein must be of sufficient magnitude so as to operate the valves. Because of this, so-called cassette type pumps have typically required a stroke volume of at least 1/15th milliliter up to as high as ¼th milliliter in order to create the proper valve action. Where, for example, it is desired to deliver a flow rate of a fluid of 1 milliliter per hour, fifteen separate pumping strokes or less, each delivering a corresponding fraction of the one milliliter volume, are required each hour. This results in an infusion rate which pulsates undesirably and may, in many instances, be unsatisfactory for producing a desired therapeutic action of the drug infused.

In an attempt to overcome the inherent limitations of the cassette type pumps described above, a syringe type pump has been devised having a relatively inexpensive syringe construction so that the syringe itself may be disposed of after each use as is done in the case of the cassette type pumps. Valve action necessary to permit filling and subsequent discharge of the syringe is accomplished by alternately pinching off and opening up tubing attached to nipples at one end of the syringe cylinder. Such a system is shown and described in U.S. Pat. No. 3,993,061, issued Nov. 23, 1976. This type of construction, however, suffers from a disadvantage that, even in simple form, the syringe itself is a relatively expensive item to be satisfactory as a disposable piece. Moreover, the syringe construction, with its plunger and cylinder design is relatively difficult to prime and is extremely slow to refill. The latter problem, in fact, may completely offset the advantage of the more continuous flow provided by the syringe construction in the first place.

It is an object of the present invention to provide an improved medical infusion system.

Another object of the invention is to provide an improved pump for use in a medical infusion system.

A further object of the invention is to provide an improved cassette, for use in a medical infusion system, which is low in cost, relatively simple of operation, and highly reliable.

Other objects of the invention will become apparent to those skilled in the art from the following description taken in connection with the accompanying drawings wherein.

Figure 1:
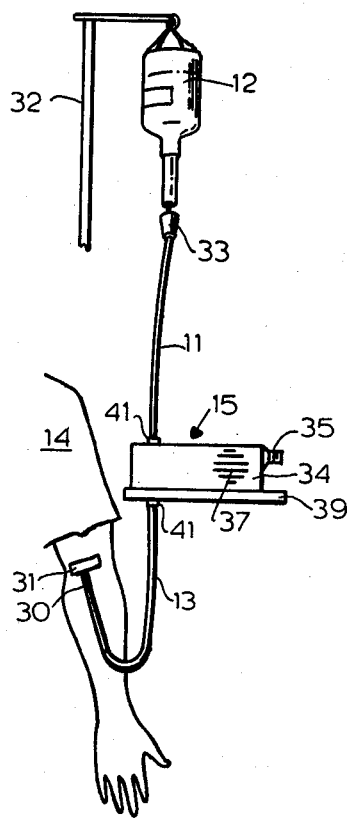
FIG. 1 is a schematic view of a medical infusion system constructed in accordance with the invention.

Very generally, the medical infusion system of the invention (FIG. 1) operates to pump fluid or semi-solids from an upstream flexible conduit portion 11 to a downstream flexible conduit portion 13. The upstream conduit portion 11 may be in fluid communication with a source 12 of fluid, and the downstream flexible conduit portion 13 may be secured suitable for delivering the fluid or semi-solid to a patient 14. The system comprises a pump 15 which includes (see FIG. 3) means 16 and 17 for supporting the conduit portions 11 and 13, respectively. First constricting means 21 are provided for selectively restricting and opening the upstream conduit portion 11. Second restricting means 22 are provided for selectively restricting and opening the downstream conduit portion 13. A replaceable cassette has means 23 and 24 detachably connected to the upstream and downstream conduit portions 11 and 13, respectively. The cassette 18 defines a pumping cavity 25 and has a flexible diaphragm 26 defining a portion of the pumping cavity. Means 27 releasably support the cassette in a position between the upstream and downstream conduit portions for connection thereto. Actuator means 28 engage the membrane and are movable from a fully retracted position (FIG. 3) to a fully extended position (FIG. 4) to displace a predetermined volume in the pumping cavity. Means 29 operate the actuator means and the first and second restricting means in a sequence such as to pump fluids or semisolids from the upstream conduit portion to the downstream conduit portion.

Referring now more particularly to FIG. 1, the invention is shown in the form of an intravenous delivery system for delivery fluid from a fluid reservoir or storage means 12 to a patient 14. The fluid is introduced intravenously through a suitable catheter 30 attached to the downstream portion 13 of the delivery system. The catheter is held in place by adhesive tape 31 on the arm of the patient 14 as is well-known in the art. The fluid reservoir 12 may be a conventional intravenous delivery system bottle suspended on a stand 32. A drip chamber 33 is attached to the lower portion of the bottle 12 and may be of conventional construction. An empty bottle alarm, not shown, of suitable design may be employed beneath or attached to the drip chamber to signal when the contents of the bottle 12 have been drained. The contents of the bottle 12 pass through the upstream conduit portion 11 of the delivery system, the upstream conduit portion constituting, in the illustrated embodiment, a flexible hose.

Although the bottle 12 is shown positioned on the support 32 in an elevated condition with respect to the patient 14, as is typical of many intravenous delivery systems, it is not critical in the system of the invention that the bottle be so elevated inasmuch as the fluid in conveyed to the patient by the positive pumping action of the pump 15. The pump 15, shown in FIG. 1, may be suitably contained in a housing 34 having control knobs including a knob 35 thereon and a vent 37 for cooling the internal contents. The pump 15 may be supported on a bedside table 39 or other suitable structure and is located between the upstream portion 11 and the downstream portion 13 of the delivery system. Grommets 41 form the entrance and the exit to the housing 33 for the upstream and downstream portions 11 and 13, respectively.

As do certain prior art systems described earlier, the system of the invention employs a replaceable cassette 18 in the pump 15. Unlike the prior art cassette type systems, however, the cassette utilized in the system of the present invention does not require any valves, vastly simplifying the system and drastically lowering the cost of the replaceable portion thereof. In addition, and unlike prior art systems employing cassettes, the system of the present invention employs a cassette in which a substantial displacement occurs during each pumping stroke. This stroke displacement in the system of the present invention is preferably about at least 0.25 ml and less than about one ml. In this range, the most acceptable performance results. Typical volume of the pumping chamber with the diaphragm in position for maximum volume is about 1.9 ml.

Figure 2:
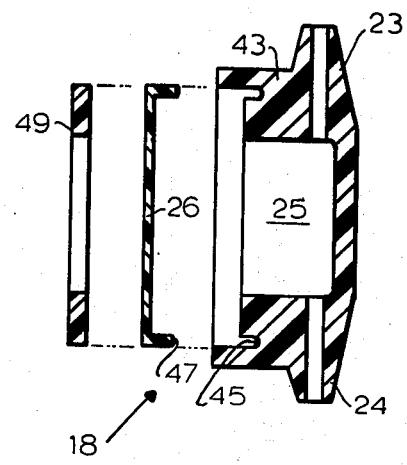
FIG. 2 is an exploded cross-sectional view of a cassette of the system of FIG. 1.

The cassette is specifically illustrated in FIG. 2. Basically, the cassette is in only three pieces. The main piece is a molded housing 43 of a suitable medical grade plastic. The outline of the housing is of generally circular shape with slightly squared but nevertheless still rounded corners. A nipple 23 is provided for connection to the upstream conduit portion of the infusion system, and a nipple 24 (on the opposite side of the housing 43) is provided for connection to the downstream conduit portion of the infusion system. Unlike many prior art cassettes, the nipples contain no valves. The housing 43 defines the pumping chamber 25 which is generally in the shape of a cylinder having one open side. An annular recess 45 surrounds the open side of the pumping chamber and receives the annular lip 47 of a flexible diaphragm 26. The diaphragm 26 is comprised of a suitable medical grade flexible material which is impervious to the fluids or semi-solids being pumped and which is capable of flexing as described below sufficiently so as to enable the desired displacement, also described in detail below. For the purpose of holding the flexible diaphragm in place, a mounting ring 49 seats in and mates with a projecting annular lip 51 on the housing 43 and is suitably sealed to the housing, such as by ultrasonic welding, to form a seal and to hold the diaphragm 26 is place spanning the open side of the pumping chamber 25.

As previously mentioned, restricting means 21 and 22 are employed to sequentially restrict and open the upstream and downstream conduit portions 11 and 13, respectively, in a sequence such as to provide a valve type action to enable fluid to be pumped from the upstream conduit portion 11 to the downstream conduit portion 13 of the delivery system. Although any suitable means for constricting the conduit portions in the manner described below may be employed, in the apparatus illustrated in FIGS. 3 and 4, the restricting means 21 and 22 are the tapered ends of movable rods or bars 63 and 65, respectively. The bars are movably supported, by suitable means not shown, inside the housing 34 of the pump 15. The rounded tips of the tapered ends 21 and 22 of the bars 63 and 65 engage the respective upstream conduit portion 11 and downstream conduit portion 13. The conduit portions are supported in mating grooves or channels in a chassis 16 inside the housing 34 of the pump 15. A boot 53 extends across the chassis 16 as shown to provide a seal between the region of the cassette 18 and the drive means described below.

Figure 4:
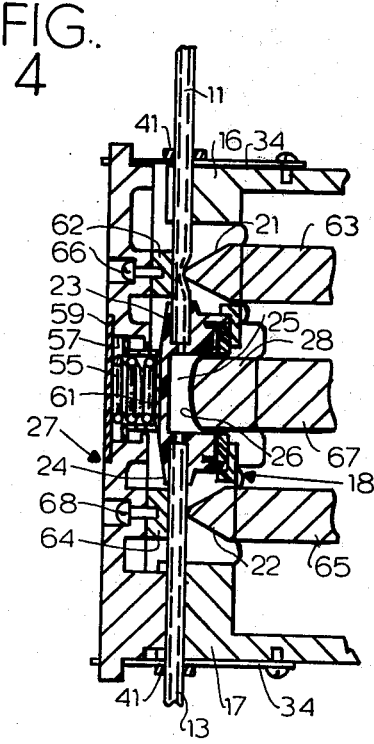

The actuator means 28 comprise the rounded end of an elongated bar 67 movably mounted in a suitable support to the chassis 16, not shown. The rounded tip of the actuator means 28 of the bar 67 engages the diaphragm 26 over the open side of the pumping chamber 25 of the cassette 18. When the cassette is properly mounted, the actuator means 28 distend the diaphragm 26 slightly inward even at maximum retraction; thus constantly being in engagement with the diaphragm throughout the pumping stroke. The volume of the pumping cavity in this maximum retracted position of the bar 67 is at its maximum operating volume. As the bar 67 moves inwardly the membrane is distended inwardly as shown in FIG. 4, thereby reducing the volume of the pumping chamber 25.

The pump 15 includes a hinged door 27 which opens to allow insertion and removal of the cassette 18 and the regions of the upstream and downstream portions 11 and 13 which are inside the pump housing 34. As may be seen in FIGS. 3 and 4 when the door 27 is closed, a coil spring 55 held in a recess 57 of the door, the latter being covered by a plate 59, presses a biasing cup 61 against the cassette housing 43, thus holding the housing in position against the chassis 16. Pressure blocks 62 and 64 are provided attached to the door 27 by adjusting screws 66 and 68, respectively. The block 62 is positioned on the opposite side of the upstream conduit portion 11 from the rod 21. Similarly, the block 64 is positioned on the opposite side of the downstream conduit portion 13 from the rod 22. By suitably adjusting the position of the blocks 62 and 64 using the screws 66 and 68, the pressure exerted by the restricting means 21 and 22 during the operation described below may be adjusted during manufacture to insure complete seal off of the tube and thus total closure, as described.

For moving the restricting means 21 and 22, and the actuator means 28 in the desired sequence, the ends of the movable bars 63, 65 and 67 opposite the cassette and conduit portions carry suitable cam followers 71 biased (by springs, not shown) against the surface of cams 91, 93 and 95. The cams 91, 93 and 95 are mounted on a cam shaft 97 which is rotated by a driving motor 103. The driving motor is a stepping motor to provide incremental rotation of the shaft and therefore incremental movement and control over the movable bars.

Figure 3:
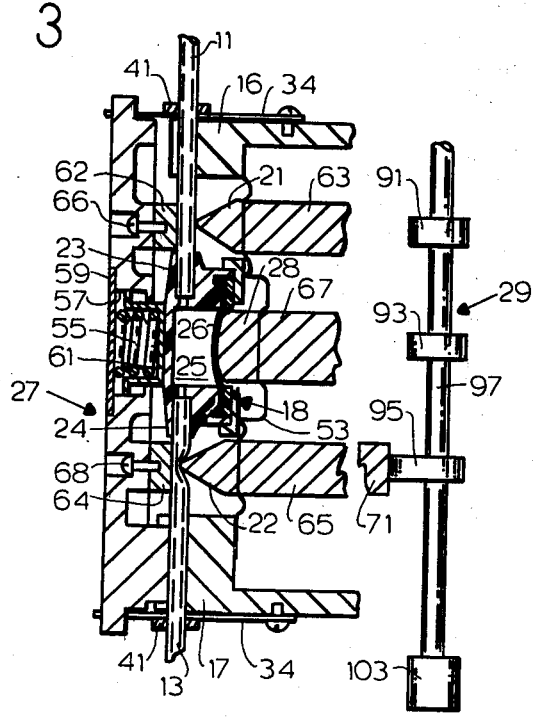
FIGS. 3 and 4 are schematic cross-sectional views illustrating the operation of the pump of FIG. 1.

In FIG. 3, the lower or second restricting means 22 is in a position such as to restrict or pinch-off the downstream flexible conduit portion 13. Due to the natural flow or pressure head of the fluid in the upstream portion, or to the suction (negative pressure) created by the retraction of the member 28, the pumping chamber 25 of the cassette 18 fills. The pumping stroke is illustrated in FIG. 4 wherein the second restricting means 22 are retracted to fully open the conduit portion 13 and the first restricting means 21 have closed to restrict or occlude the upstream conduit portion 11. Movement of the actuator means 28 inwardly reduces the volume of the pumping chamber 25 causing at least some of the contents to be expelled toward the downstream portion of the delivery system. The distance which the actuator means 25 move inwardly determines the displacement volume during the pumping stroke. The filling and pumping strokes are conducted in sequence and repeated according to the rotation of the cam shaft 97 and the configuration of the cams 91, 93 and 95.

Figure 5:
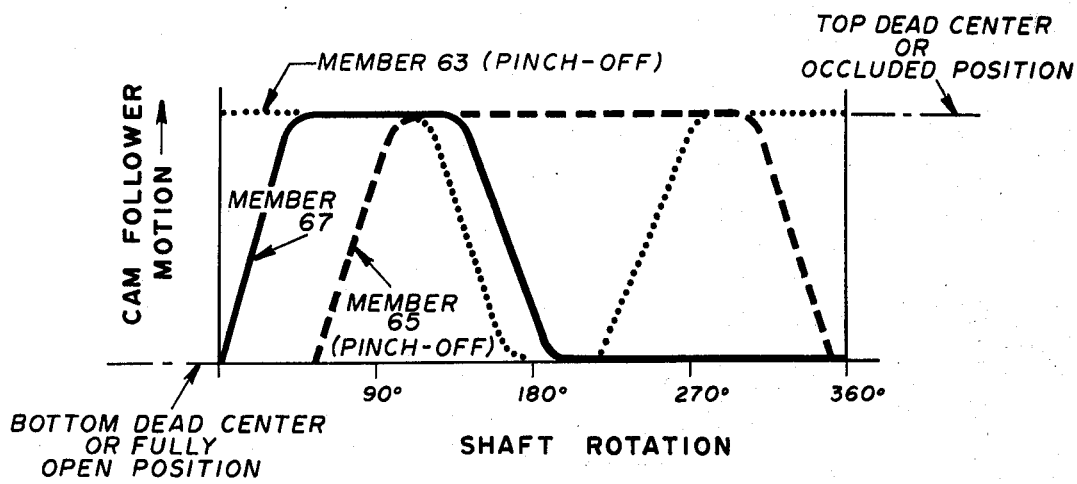
FIG. 5 is a graph illustrating the operation of the cam driving means illustrated in FIG. 3.

Referring to FIG. 5, a plot is provided illustrating the motion versus degrees of shaft rotation for the three sliding bars 63, 65 and 67, respectively. At the left-hand edge position or 0° position shown in the plot, the upstream bar 63 is closed whereas the bars 65 and 67 are open. Movement of the bar 67 from the fully open position to the occluded position displaces a precise predetermined amount of the contents of the pumping chamber 25. Following this movement, the bar 65 moves to the occluded position to close the downstream conduit portion 13. Once this occurs, the bar 63 moves to the open position as does the bar 67, allowing filling of the pumping chamber once again. Between 180° and 270°, the upstream movable bar 63 moves from the open position to the closed position, and between 270° and 360° the downstream movable bar 65 moves to the open position. This places the system in readiness for the next displacement stroke beginning with 0°.

Figure 6:
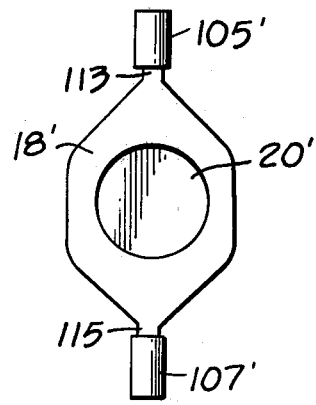
FIG. 6 is a top plan view of an alternate configuration of a cassette for the system of FIG. 1.
Figure 7:
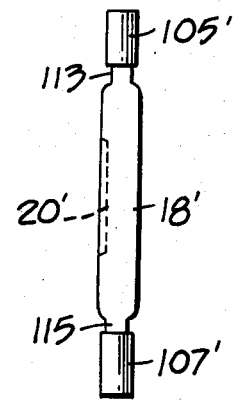
FIG. 7 is a side view of the cassette of FIG. 6.

Referring now to FIGS. 6 and 7, an alternate configuration for the cassette of the pump is shown. The cassette 18' is of a flatter configuration from that of FIG. 2, defining a pancake-shaped pumping cavity. The diaphragm 20° is formed by a membrane spanning the window. Inlet and outlet nipples 113 and 115 are formed integrally with the cassette 18', and flexible sleeves 105' and 107' are attached thereto, forming the upstream and downstream flexible conduit portions. The nipples 113 and 115 contain no valves.

Typical applications of the invention would involve maximum pressures of about 25 psi. Accordingly, the "rigidity" of the cassette 18 is selected appropriately. It is preferred that the actuator means engage the diaphragm throughout its stroke, and that there always be a slight inward loading on the diaphragm. For satisfactory accuracy, it is preferred that the unsupported or unengaged area of the diaphragm not exceed 75 percent of the total diaphragm (window) area Rather than the cam drive illustrated, other means for operating the restricting means may be utilized, such as a lead screw drive. However, incremental control over the diaphragm movement is significant in achieving proper accuracy and control. By suitable design, a desired displacement volume may be selected for each step. Digital control is then readily possible with commercially available and relatively inexpensive microcomputer chips. Functions such as flow rate, total volume delivered and flow error monitoring may easily be handled by known digital techniques.

It is usually preferable to design the system to operate such that the return strokes, i.e. filling strokes, be of the same duration regardless of the delivery rate and volume. Thus, the flow may be more even where the actuator means are retracted at a relatively quick fixed rate as opposed to a varying inward (delivery) rate. Digital capability makes such operation easily achievable.

The size of the outlet and inlet openings relative to the diaphragm size is of significance. With inlet and outlet openings which are too large, regurgitation becomes a large enough factor to deleteriously affect accuracy. Thus, it is preferred that each of the inlet and outlet openings have a cross-sectional area having a ratio to the diaphragm or window area of not greater than about 0.3.

As is the case with any cassette type pump, the presence of air in the cassette can affect the accuracy of the pumping rate. To avoid such problems, two solutions are available. In the first, a large displacement to volume ratio is used. If the displacement volume is at least 50 percent of the starting operating volume of the pumping chamber, most air entering the cassette will be pushed out and may be readily detected by an air detector or trapped in an air trap downstream of the cassette. The second solution is to orient the cassette so that the outlet nipple is above the inlet nipple. This also insures that any air entering the cassette will be expelled by the membrane stroke.

In addition to the foregoing, the medical infusion system of the invention provides other significant advantages over many prior art constructions. There are no valves employed in the cassette, thus significantly improving the reliability and reducing the complexity of manufacture and therefore the cost. Increased accuracy over prior cassette designs is also achieved. By properly designing the cams and the size of the movable restricting elements, good constant flow rates may be achieved, even to very low rates. For example, the system of the invention is capable of delivering at a one ml per hour flow rate with an incremental delivery of every 26 seconds and a refill time of only one second.

Various modifications of the invention in addition to those shown and described herein will become apparent to those skilled in the art from the foregoing description and accompanying drawings. Such modifications are intended to fall within the scope of the appended claims.

What is claimed is:

1. A medical infusion system for pumping fluids or semi-solids from an upstream flexible conduit portion of the infusion system to a downstream flexible conduit portion thereof, comprising, a pump having means for supporting said conduit portions, first constricting means for selectively restricting and opening said upstream conduit portion, second restricting means for selectively restricting and opening said downstream conduit portion, a cassette having means for connecting to said upstream and downstream conduit portions, said cassette comprising a rigid enclosure defining a substantially cylindrical pumping cavity having an open end defining a window and having valveless inlet and outlet openings, the cross-sectional area of each of said inlet and outlet openings having a ratio to the area of said window not greater than about 0.3 to 1, a diaphragm relatively more flexible than said enclosure extending and held in fluid tight engagement across said window and being impermeable to the passage of fluids or semi-solids therethrough, means for releasably supporting said cassette in a position between said upstream and downstream conduit portions in connection therewith, actuator means for engaging said diaphragm and being movable to displace, from a fully retracted position to a fully extended position, a predetermined volume in said pumping cavity, said actuator means being of a size such that the area of said diaphragm not engaged with said actuator means is less than about three-quarters of the total area of said diaphragm, said predetermined volume being at least about 0.25 ml and less than about 1.01 ml, and means for operating said first and second restricting means and said actuator means in a sequence such as to pump fluids or semi-solids from said upstream conduit portion to said downstream conduit portion.

2. A medical infusion system according to claim 1 wherein said operating means include drive means for providing incremental movement of said actuator means from the fully retracted position to the fully extended position to control incrementally the displacement of said predetermined volume in said pumping cavity.

3. A medical infusion system according to claim 1 wherein said cassette comprises a cassette housing having inlet and outlet openings for communicating with said upstream and downstream conduit portions, respectively, and defining said pumping cavity with a window opening thereon, said diaphragm spanning said window and having a peripheral portion extending beyond the periphery of said window and having an annular rib thereon adjacent the periphery thereof, said rigid enclosure having an annular recess for mating with said annular rib on said diaphragm, and a mounting ring secured to said housing and clamping said peripheral portion of said diaphragm against said housing to form a seal therewith.

4. A medical infusion system according to claim 1 wherein said means for releasably supporting said cassette include a door on said pump movable to a closed position covering said cassette, said door having a spring biased member thereon for engaging said cassette when said door is in a closed position.

5. A replaceable pump cassette for use in a pump for a medical infusion system which pumps fluid or semi-solids from an upstream portion of the infusion system to a downstream portion thereof, said cassette comprising, a rigid enclosure defining a substantially cylindrical pumping cavity having an open end defining a window, a first nipple defining an inlet opening communicating with said cavity and a second nipple defining an outlet opening communicating with said cavity, said nipples being absent any valves and providing for connecting said inlet and outlet openings to the upstream and downstream portions, respectively of the medical infusion system, a diaphragm relatively more flexible than said enclosure extending and held in fluid tight engagement across said window and being impermeable to the passage of fluid or semi-solids therethrough, and a locking ring secured to said enclosure and clamping said diaphragm in position at the periphery thereof, said diaphragm having an annular rib thereon adjacent the periphery thereof, said rigid enclosure including an annular recess for mating with said annular rib on said diaphragm, said locking ring being positioned against said diaphragm on the opposite side from said annular rib, said inlet opening and said outlet openings each having a cross-sectional area having a ratio to the area of said window of less than about 0.3.

* * * * *